United States Patent
Zhou

(10) Patent No.: US 10,378,119 B2
(45) Date of Patent: *Aug. 13, 2019

(54) PLATINUM ELECTRODE SURFACE COATING AND METHOD FOR MANUFACTURING THE SAME

(75) Inventor: Dao Min Zhou, Saugus, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 970 days.

This patent is subject to a terminal disclaimer.

(21) Appl. No.: 11/506,618

(22) Filed: Aug. 17, 2006

(65) Prior Publication Data

US 2007/0089994 A1    Apr. 26, 2007

Related U.S. Application Data

(62) Division of application No. 11/259,822, filed on Oct. 26, 2005.

(51) Int. Cl.
*C25D 3/50* (2006.01)
*A61N 1/05* (2006.01)

(52) U.S. Cl.
CPC .................. *C25D 3/50* (2013.01); *A61N 1/05* (2013.01)

(58) Field of Classification Search
CPC ............... C25D 3/50; B23H 3/04; A61N 1/18
USPC ........................................................ 205/264
See application file for complete search history.

(56) References Cited

U.S. PATENT DOCUMENTS

| | | | | |
|---|---|---|---|---|
| 2,792,341 A | * | 5/1957 | Atkinson | 205/264 |
| 3,309,292 A | * | 3/1967 | Andrews | C25D 3/66 205/103 |
| 3,865,697 A | * | 2/1975 | Suggs | 205/117 |
| 4,240,878 A | | 12/1980 | Carter | |
| 4,427,502 A | * | 1/1984 | Abys | C25D 3/52 205/242 |
| 4,981,573 A | * | 1/1991 | Klotz et al. | 205/483 |
| 5,109,844 A | | 5/1992 | De Juan, Jr. et al. | |
| 5,571,158 A | | 11/1996 | Bolz et al. | |
| 5,609,611 A | | 3/1997 | Bolz et al. | |
| 5,632,770 A | | 5/1997 | Schaldach | |

(Continued)

FOREIGN PATENT DOCUMENTS

JP    2005241622 A   *  9/2005   ............. G01N 27/30

OTHER PUBLICATIONS

Pavlovic et al., "On the Use of Platinized and Activated Titanium Anodes in Some Electrodeposition Processes", J. Solid State Electrochem (no month, 1997), vol. 1, pp. 208-214.*

(Continued)

*Primary Examiner* — Edna Wong
(74) *Attorney, Agent, or Firm* — Scott Dunbar

(57) ABSTRACT

An electrode surface coating and method for manufacturing the electrode surface coating comprising a conductive substrate; a surface coating of platinum having a rough configuration and an increase in the surface area of 5 times to 500 times of the corresponding surface area resulting from the basic geometric shape of the electrode. A method for electroplating an electrode surface with platinum coating having a rough surface, comprising electroplating the surface of a conductive substrate at a rate such that the metal particles form on the conductive substrate faster than necessary to form shiny platinum and slower than necessary to form platinum black.

5 Claims, 9 Drawing Sheets

(56) References Cited

U.S. PATENT DOCUMENTS

| | | | |
|---|---|---|---|
| 5,822,177 A | 10/1998 | Popp et al. | |
| 5,871,511 A | 2/1999 | Bolz et al. | |
| 5,935,155 A | 8/1999 | Humayan et al. | |
| 5,964,794 A | 10/1999 | Bolz et al. | |
| 6,219,581 B1 | 4/2001 | Schaldach et al. | |
| 6,230,061 B1 | 5/2001 | Hartung | |
| 6,292,703 B1 | 9/2001 | Meier et al. | |
| 6,522,924 B1 | 2/2003 | Meier | |
| 6,974,533 B2 * | 12/2005 | Zhou | A61N 1/0543 205/264 |
| 7,142,909 B2 * | 11/2006 | Greenberg | A61N 1/0543 607/2 |
| 2003/0192784 A1 * | 10/2003 | Zhou | A61N 1/0543 205/109 |
| 2003/0233134 A1 * | 12/2003 | Greenberg et al. | 607/36 |
| 2007/0092786 A1 * | 4/2007 | Zhou | 429/44 |

OTHER PUBLICATIONS

"Platinized Platium Electrodes", A.M. Feltham and M. Spiro, Department of Chemistry, Imperial College of Science and Technology, London S.W.7, England; Chemical Reviews, 1971, vol. 71, No. 2; pp. 178-193.

"Fractal Coated Leads: Advanced Surface Technology of Genuine Sensing and Pacing", M. Schaldach, Department of Biomedical Engineering, Erlangen-Nuremberg, Germany Progress in Biomedical Research, Jun. 2000; pp. 259-272.

* cited by examiner

PLATINUM ELECTRODE SURFACE COATING AND METHOD FOR MANUFACTURING THE SAME

CROSS-REFERENCE TO RELATED APPLICATION(S)

This patent application is a divisional application of U.S. patent application Ser. No. 11/259,822, filed Oct. 26, 2005, now US Pat. No. 7,887,681, the disclosure of which is incorporated herein by reference.

FEDERALLY SPONSORED RESEARCH

This invention was made with government support under grant No.: R24EY12893-01, awarded by the National Institutes of Health. The government has certain rights in the invention.

BACKGROUND OF THE INVENTION

Field of the Invention

The field of the invention relates to platinum electrode surface coating and electroplating processes for deposition of surface coating.

Description of Related Art

Platinum has often been used as a material for electrodes in corrosive environments such as the human body due to its superior electrical characteristics, biocompatibility and stability. Platinum has many desirable qualities for use as an electrode for electrical stimulation of body tissue. Since platinum has a smooth surface and its surface area is limited by the geometry of the electrode, it is not efficient for transferring electrical charge. The platinum with a smooth surface is hereinafter called "shiny platinum".

Electrodes for stimulating body tissue by electrical stimulation are known in great variety. For the utility of an implantable stimulation or sensing electrode—especially one intended for long-term use in a tissue stimulator with a non-renewable energy source and that, therefore, must require minimal energy—a high electrode capacitance and correspondingly low electrical impedance is of great importance. Furthermore, without sufficiently low impedance, a large voltage may cause polarization of both the electrode and the tissue to which the electrode is attached forming possibly harmful byproducts, degrading the electrode and damaging the tissue.

Because the ability of an electrode to transfer current is proportional to the surface area of the electrode and because small electrodes are necessary to create a precise signal to stimulate a single nerve or small group of nerves, many in the art have attempted to improve the ability of an electrode to transfer charge by increasing the surface area of the electrode without increasing the size of the electrode.

One approach to increase the surface area of a platinum electrode without increasing the electrode size and therefore to improve the ability of the electrode to transfer charge is to electroplate platinum rapidly such that the platinum molecules do not have time to arrange into a smooth, shiny surface. The rapid electroplating forms a platinum surface which is commonly known as "platinum black". Platinum black has a porous and rough surface which is less dense and less reflective than shiny platinum. U.S. Pat. No. 4,240,878 to Carter describes a method of plating platinum black on tantalum.

Platinum black is more porous and less dense than shiny platinum. Platinum black has weak structural and physical strength and is therefore not suitable for applications where the electrode is subject to even minimal physical stresses. Platinum black also requires additives such as lead to promote rapid plating. Lead, however, is a neurotoxin and cannot be used in biological systems. Finally, due to platinum black's weak structure, the plating thickness is quite limited. Thick layers of platinum black simply fall apart.

The US patent application No. 2003/0192784 "Platinum Electrode and Method for Manufacturing the Same" to Dao Min Zhou filed Aug. 23, 2002, the disclosure of which is incorporated herein by reference, discloses an electrode comprising an electrode body; and a surface coating of platinum having a fractal configuration.

The US patent application No. 2003/0233134 "Biocompatible Bonding Method and Electronics Package Suitable for Implantation" to Robert J. Greenberg et al. filed Sep. 6, 2002, the disclosure of which is incorporated herein by reference, discloses a device comprising a substrate at least a portion of which is electrically conductive; a flexible assembly; and at least one deposited rivet that bonds said substrate and said flexible assembly together.

The US patent application No. 2004/0220652 "Adherent Metal Oxide Coating Forming a High Surface Area Electrode" to Dao Min Zhou et al. filed Nov. 4, 2004, the disclosure of which is incorporated herein by reference, discloses an implantable electrode comprising: a roughened conductive substrate; and a rough surface coating on said substrate.

There is a further need for an alternative electroplating of a thinner surface with platinum to obtain an increased surface area for a given geometry and at the same time the coating is structurally strong enough to be used in applications where the platinum surface coating is subject to physical stresses.

SUMMARY OF THE INVENTION

The present invention is directed in part to an electrode surface coating having increased surface area for greater ability to transfer charge and also having sufficient physical and structural strength to withstand physical stress.

This and other aspects of the present invention which may become obvious to those skilled in the art through the following description of the invention are achieved by an improved surface coating and method for preparing the improved surface coating having a rough surface comprising one or more of the following metals titanium, niobium, tantalum, ruthenium, rhodium, iridium, palladium, platinum, or gold, or an alloy of two or more metals, or a combination of two or more alloys or metal layers thereof having an increase in the surface area of 5 times to 500 times of the corresponding surface area resulting from the basic geometric shape.

The coating of the present invention has an increase in surface area of at least 5 times compared to shiny platinum of the same geometry. The coating of the present invention has at the same time an improved resistance to physical stress when compared to platinum black.

The process of electroplating the surface coating of the present invention comprises plating at a rate that is faster than the rate necessary to produce shiny platinum and that is less than the rate necessary to produce platinum black.

DETAILED DESCRIPTION OF THE INVENTION

The present invention is directed in part to an electrode surface coating having increased surface area for greater ability to transfer charge and also having sufficient physical and structural strength to withstand physical stress.

The electrode surface coating is achieved by an improved surface coating and method for preparing the improved surface coating having a rough surface comprising platinum having a rough configuration and an increase in the surface area of 5 times to 500 times of the corresponding surface area resulting from the basic geometric shape of the electrode.

The conductive substrate comprises one or more of the following metals titanium, zirconium, niobium, tantalum, ruthenium, rhodium, iridium, palladium, platinum, silver, gold or carbon.

The conductive substrate comprises preferably palladium, platinum, iridium, gold, tantalum, titanium, titanium nitride or niobium.

The process of electroplating an electrode surface coating having a rough surface comprises electroplating the surface of a conductive substrate at a rate such that the metal particles form on the conductive substrate faster than necessary to form shiny metal and slower than necessary to form metal black. A method for electroplating an electrode surface coating having a rough surface, comprises electroplating the surface of a conductive substrate with platinum at a rate such that the metal particles form on the conductive substrate faster than necessary to form shiny platinum and slower than necessary to form platinum black.

Figure 1:
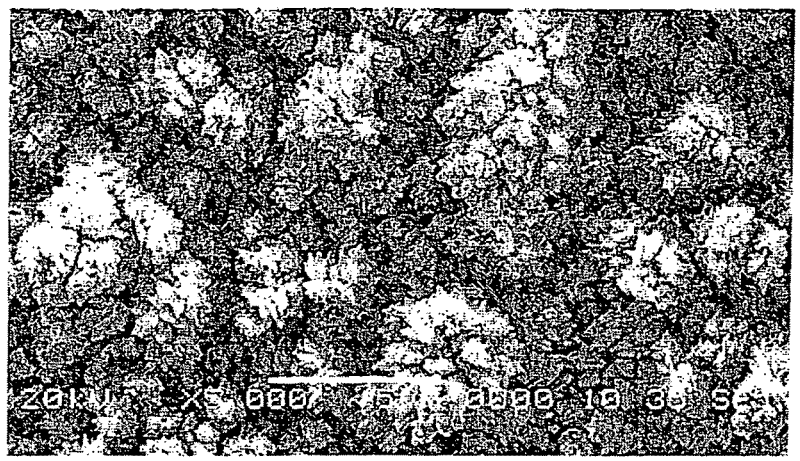
FIG. 1 shows a platinum gray surface magnified 5000 times.
Figure 2:
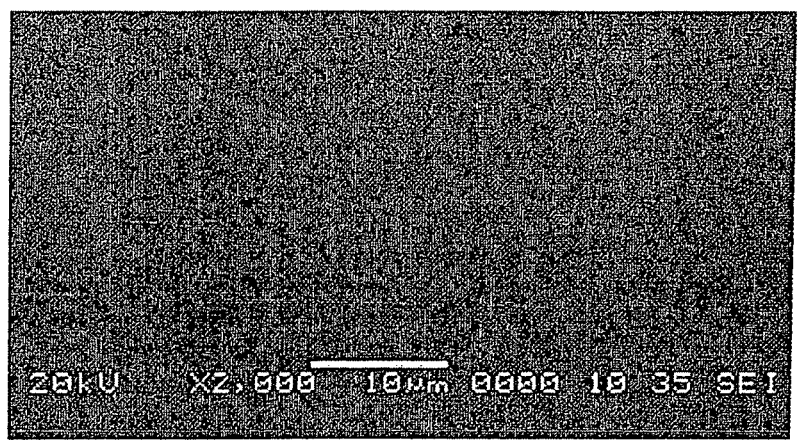
FIG. 2 shows a shiny platinum surface magnified 2000 times.
Figure 3:
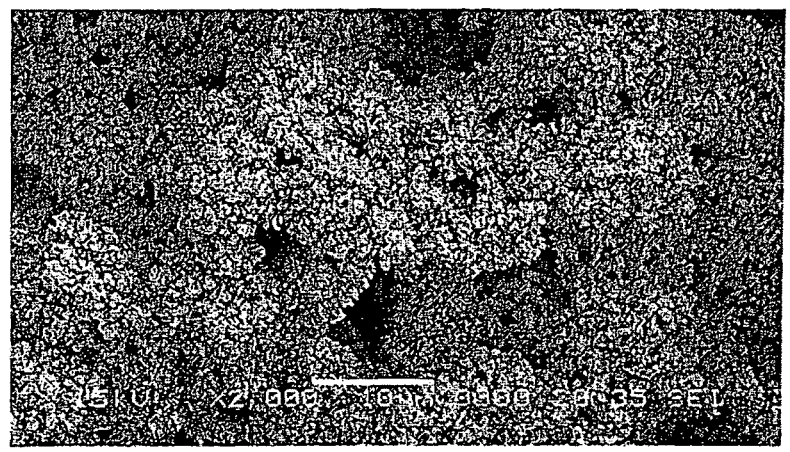
FIG. 3 shows a platinum black surface magnified 2000 times.

FIGS. 1, 2, and 3 are images produced on a Scanning Electron Microscope (SEM). FIG. 1 at 5000× and FIGS. 2 and 3 at 2000× are magnifications taken by a JEOL JSM5910 microscope (Tokyo, Japan). FIG. 1 shows an illustrative example of a platinum gray surface coating for an electrode having a fractal surface with a surface area increase of greater than 5 times the surface area for a shiny platinum surface of the same geometry, shown in FIG. 2, and an increase in strength over a platinum black surface, shown in FIG. 3. Under the magnification level of 5000 it is observed that platinum gray is of a fractal configuration having a cauliflower shape with particle sizes ranging from 0.5 µm to 15 µm. Each branch of such structure is further covered by smaller and smaller particles of similar shape. The smallest particles on the surface layer may be in the nanometer range. This rough and porous fractal structure increases the electrochemically active surface area of the platinum surface when compared to an electrode with a smooth platinum surface having the same geometric shape.

The surface is pure platinum because no impurities or other additives such as lead need to be introduced during the plating process to produce platinum gray. This is especially advantages in the field of implantable electrodes because lead is a neurotoxin and cannot be used in the process of preparing implantable electrodes. Alternatively, other materials such as iridium, rhodium, gold, tantalum, titanium or niobium could be introduced during the plating process if so desired but these materials are not necessary to the formation of platinum gray.

Platinum gray can also be distinguished from platinum black and shiny platinum by measuring the color of the material on a spectrodensitometer using the Commission on Illumination L*a*b* color scale. L* defines lightness, a* denotes the red/green value and b*, the yellow/blue value. The lightness value (called L* Value) can range from 0 to 100, where white is 100 and black is 0—similar to grayscale. The a* value can range from +60 for red and −60 for green, and the b* value can range from +60 for yellow and −60 for blue. All samples measured have very small a* and b* values (they are colorless or in the so called neutral gray zone), which suggests that the lightness value can be used as grayscale for Platinum coatings.

Figure 4:
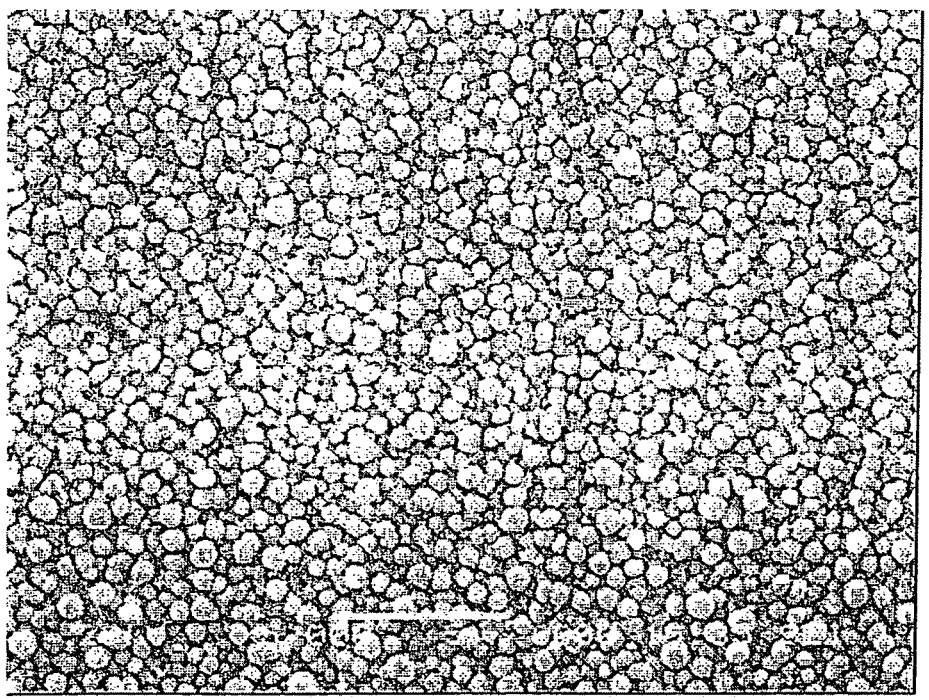
FIG. 4 shows SEM of an electroplated platinum rough surface at −0.525 V magnified 5000 times.

FIG. 4 shows an illustrative example of a platinum surface coating for an electrode having a rough surface with a surface area increase of greater than 5 times the surface area for a platinum surface of the same geometry. Under the magnification of 5000 times it is observed that the platinum is of a rough configuration having a regular shape with particle sizes ranging from 0.1 µm to 2.0 µm and has an average size of 0.4 µm to 0.6 µm, preferably about 0.5 µm. The thickness of the coating is 0.1 µm to 5.0 µm, preferably 1.0 µm to 4.0 µm, more preferably 3.3 µm to 3.8 µm. Some rough features with a scale in the nanometer range were present on each particle. The plated platinum layer is not believed to be porous. The bead shaped platinum particles with nanometer rough features on the particles increase the electrode's electrochemical active surface. The electrochemical capacitance of the electrode array with the surface coating of rough platinum is about 1300 µF/cm$^2$ to 1500 µF/cm$^2$, measured in a 10 mM phosphate buffered saline solution. The relation of the platinum surface area to the thickness of the platinum surface coating is of 4.0 F/cm$^3$ to 5.0 F/cm$^3$. The thin-film platinum disks have an average capacitance of less than 20 µF/cm$^2$ before plating, measured at the same condition. The electrochemical active surface area increase is 70 to 80, preferably about 71 to 75 fold.

The SEM/EDX analysis confirms that plated surface contains pure platinum. The surface is pure platinum because no impurities or other additives such as lead need to be introduced during the plating process to produce this platinum.

The electroplating process with platinum can be preferably performed in an aqueous solution containing sodium dihydrogen phosphate ($NaH_2PO_4$) and/or disodium hydrogen phosphate ($Na_2HPO_4$) and platinum tetra chloride ($PtCl_4$) at 20° C. to 40° C. Different concentrations of platinum can be used and the range of platinum salt concentrations can be from 1 to 30 mM. Other Pt salts will also produce similar results.

Figure 5:
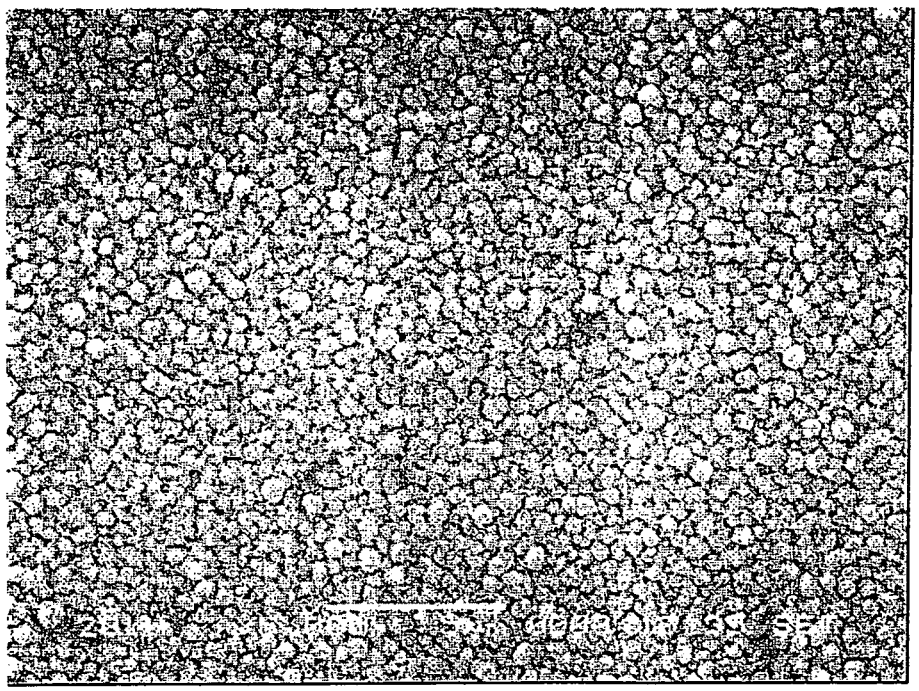
FIG. 5 shows SEM of an electroplated platinum rough surface at −0.5 V magnified 5000 times.

FIG. 5 shows an illustrative example of a platinum surface coating for an electrode having a rough surface with a surface area increase of greater than 5 times the surface area for a platinum surface of the same geometry. Under the magnification of 5000 times it is observed that the platinum is of a rough configuration having a regular shape with particle sizes ranging from 0.1 μm to 2.0 μm and has an average size of 0.4 μm to 0.6 μm, preferably about 0.5 μm. The thickness of the coating is 0.1 μm to 4.0 μm, preferably 2.0 μm to 3.0 μm, more preferably 2.3 μm to 2.8 μm. Some rough features with a scale in the nanometer range were present on each particle. The plated platinum layer is not believed to be porous. The bead shaped platinum particles with nanometer rough features on the particles increased electrode's electrochemical active surface. The electrochemical capacitance of the electrode array with the surface coating of rough platinum is about 1150 $\mu F/cm^2$ to 1680 $\mu F/cm^2$, measured in a 10 mM phosphate buffered saline solution. The relation of the platinum surface area to the thickness of the platinum surface coating is of 5.0 $F/cm^3$ to 6.0 $F/cM^3$. The thin-film platinum disks have an average capacitance of less than 20 $\mu F/cm^2$ before plating, measured at the same condition. The electrochemical active surface area increase is 65 to 75, preferably about 68 to 72 fold.

The SEM/EDX analysis confirms that plated surface contains pure platinum. The surface is pure platinum because no impurities or other additives such as lead need to be introduced during the plating process to produce this platinum.

The relation of the platinum surface area to the thickness of the platinum surface coating is of 4.0 $F/cm^3$ to 5.0 $F/cm^3$ as referred to in FIG. 4 and of 5.0 $F/cm^3$ to 6.0 $F/cm^3$ as referred to in FIG. 5. FIGS. 4 and 5 both depict a rough surface platinum coating according to the present invention. This value is calculated by dividing the electrochemically active platinum surface area ($\mu F/cm^3$) by the thickness of the platinum coating (μm). In comparison to the rough surface platinum coating the fractal platinum coating as referred to in FIG. 1 has a relation of the platinum surface area to the thickness of the platinum surface coating of 0.8 $F/cm^3$ to 1.5 $F/cm^3$. The rough platinum coating of the present invention yields on the same electrochemically active surface area a thinner coating with a higher capacitive volume compared with platinum gray.

Figure 6:
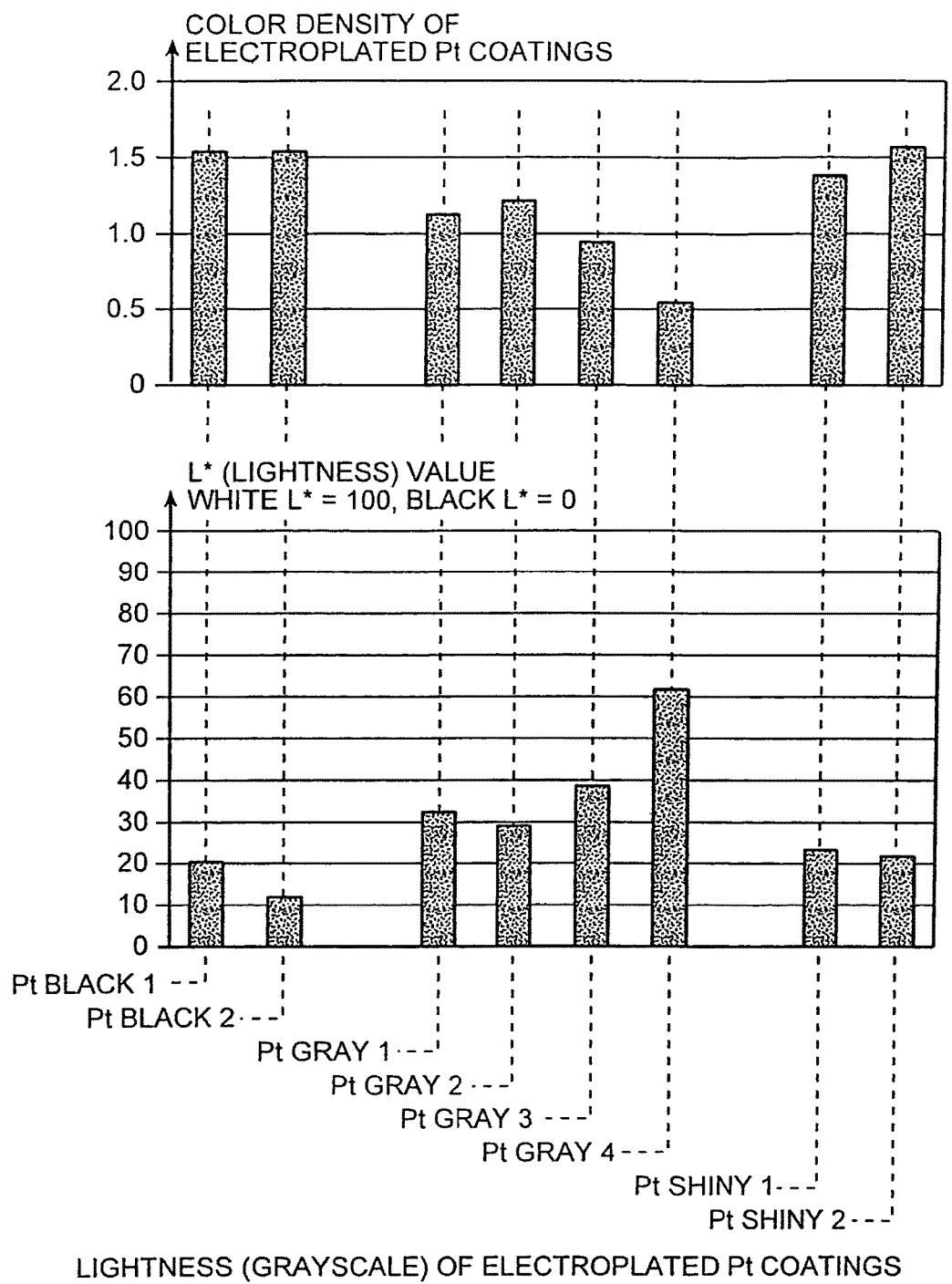
FIG. 6 shows color density (D) values and lightness (L*) values for several representative samples of platinum gray, platinum black and shiny platinum.

FIG. 6 shows the L*, a*, and b* values for representative samples of platinum gray, platinum black and shiny platinum as measured on a color reflection spectrodensimeter, X-Rite 520. Platinum gray's L* value ranges from 25 to 90, while platinum black and shiny platinum both have L* values less than 25. Measurements of color densities for representative samples of platinum gray, platinum black and shiny platinum are shown in FIG. 6 as well. Platinum gray's color density values range from 0.4D to 1.3D; while platinum black and shiny platinum both have color density values greater than 1.3D.

Platinum gray can also be distinguished from platinum black based on the adhesive and strength properties of the thin film coating of the materials. Adhesion properties of thin film coatings of platinum gray and platinum black on 500 μm in diameter electrodes have been measured on a Micro-Scratch Tester (CSEM Instruments, Switzerland). A controlled micro-scratch is generated by drawing a spherical diamond tip of radius 10 μm across the coating surface under a progressive load from 1 mN to 100 mNs with a 400 μm scratch length. At a critical load the coating will start to fail. Using this test it is found that platinum gray can have a critical load of over 60 mNs while platinum black has a critical load of less than 35 mNs.

FIGS. 7, 8, 9 and 10 show a method to produce platinum gray according to the present invention comprising connecting a platinum electrode 2, the anode, and a conductive substrate to be plated 4, the cathode, to a power source 6 with a means of controlling and monitoring 8 either the current or voltage of the power source 6. The anode 2, cathode 4, a reference electrode 10 for use as a reference in controlling the power source 6 and an electroplating solution are placed in an electroplating cell 12 having a means 14 for mixing or agitating the electroplating solution. Power is supplied to the electrodes with constant voltage, constant current, pulsed voltage, scanned voltage or pulsed current to drive the electroplating process. The power source 6 is modified such that the rate of deposition will cause the platinum to deposit as platinum gray, the rate being greater than the deposition rate necessary to form shiny platinum and less than the deposition rate necessary to form platinum black.

Figure 7:
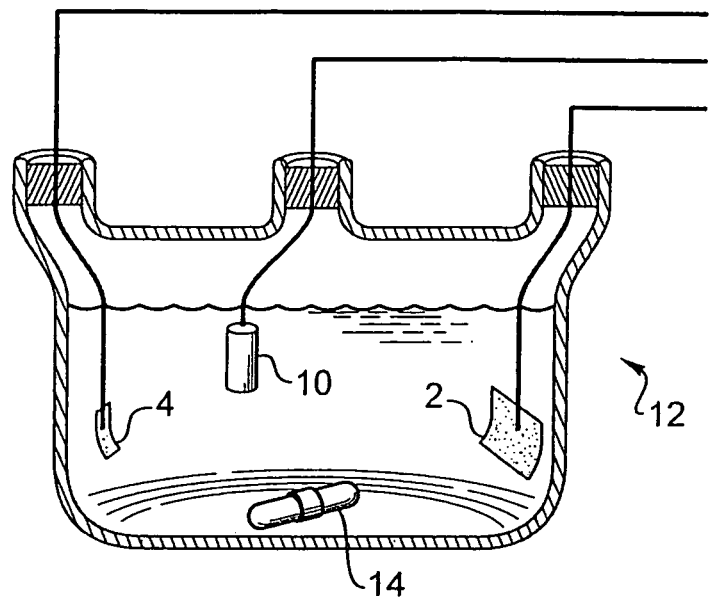
FIG. 7 shows a three-electrode electroplating cell with a magnetic stirrer.
Figure 8:
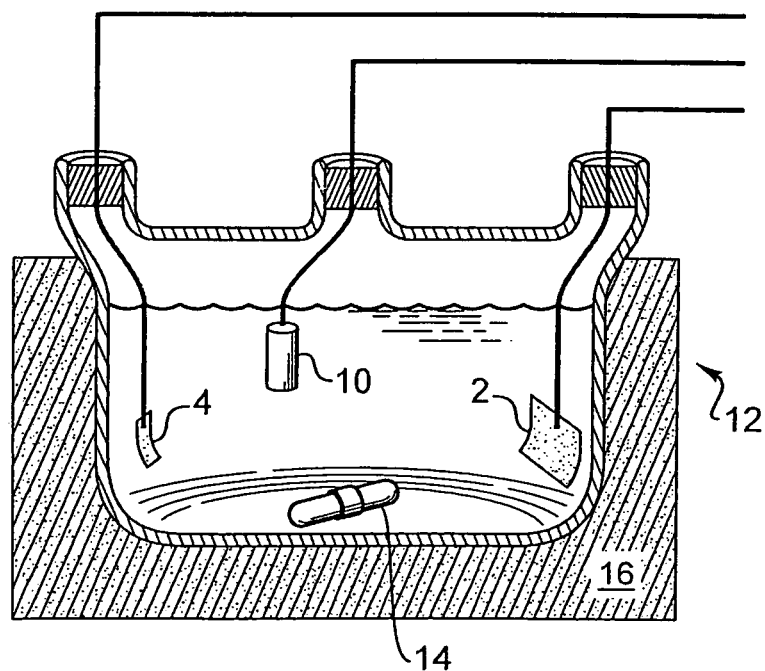
FIG. 8 shows a three-electrode electroplating cell in an ultrasonic tank.
Figure 9:
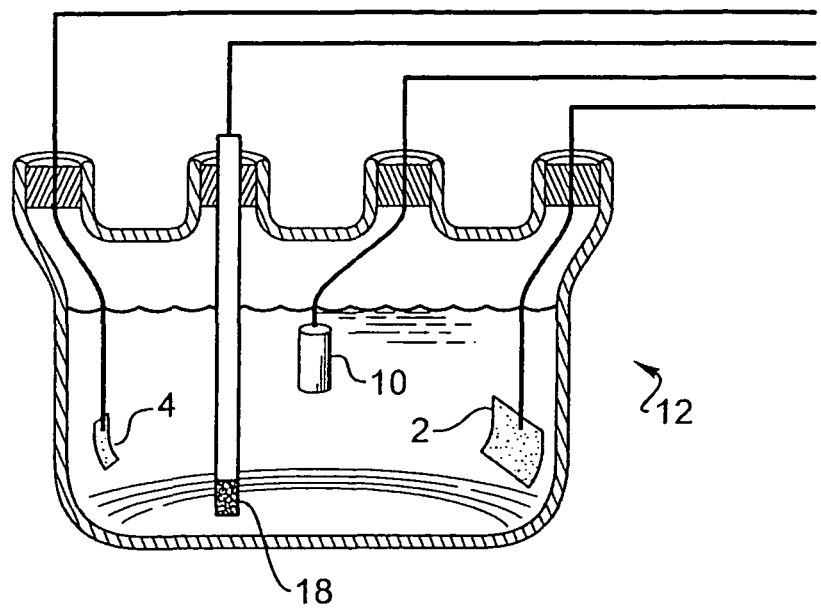
FIG. 9 shows a three-electrode electroplating cell with a gas dispersion tube.

FIGS. 7, 8 and 9 show that the electroplating cell 12, is preferably a 50 ml to 150 ml four neck glass flask or beaker, the common electrode 2, or anode, is preferably a large surface area platinum wire or platinum sheet, the reference electrode 10 is preferably a Ag/AgCl electrode (silver, silver chloride electrode), the conductive substrate to be plated 4, or cathode, can be any suitable material depending on the application and can be readily chosen by one skilled in the art. Preferable examples of the conductive substrate to be plated 4 include but are not limited to platinum, iridium, rhodium, gold, tantalum, titanium or niobium.

The stirring mechanism is preferably a magnetic stirrer 14 as shown in FIG. 7, an ultrasonic tank 16 (such as the VWR Aquasonic 50D) as shown in FIG. 8, or gas dispersion 18 with Argon or Nitrogen gas as shown in FIG. 7. The plating solution is preferably 3 to 30 mM ammonium hexachloroplatinate in disodium hydrogen phosphate, but may be derived from any chloroplatinic acid or bromoplatinic acid or other electroplating solution. The preferable plating temperature is approximately 24 ° C. to 26 ° C.

Figure 10:
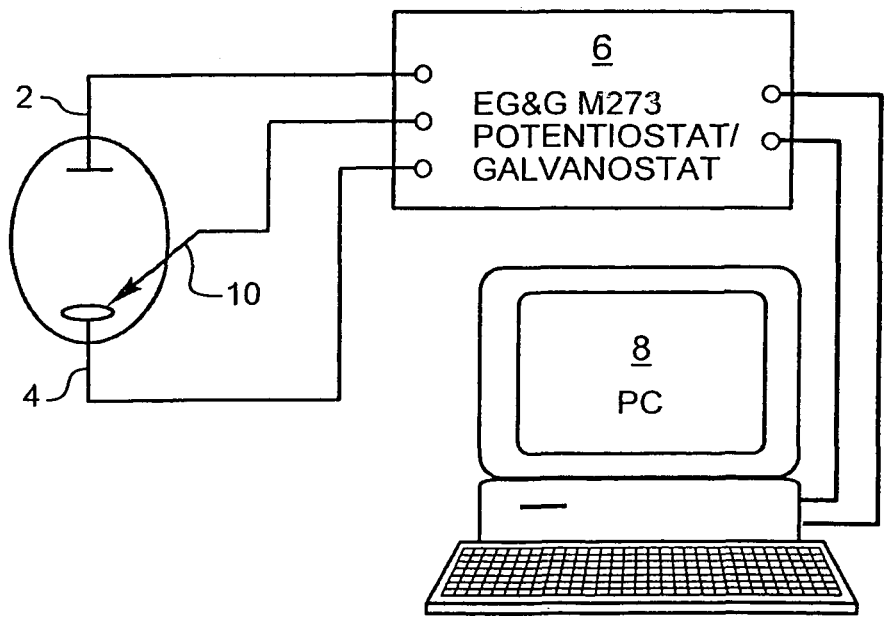
FIG. 10 shows an electroplating system with constant voltage control or constant current control.
Figure 11:
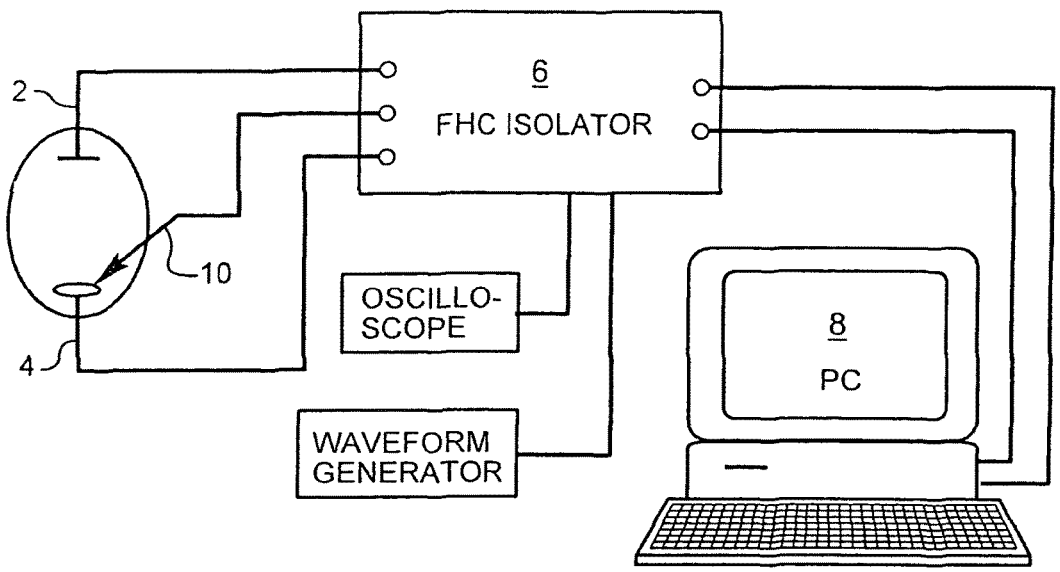
FIG. 11 shows an electroplating system with pulsed current control.
Figure 12:
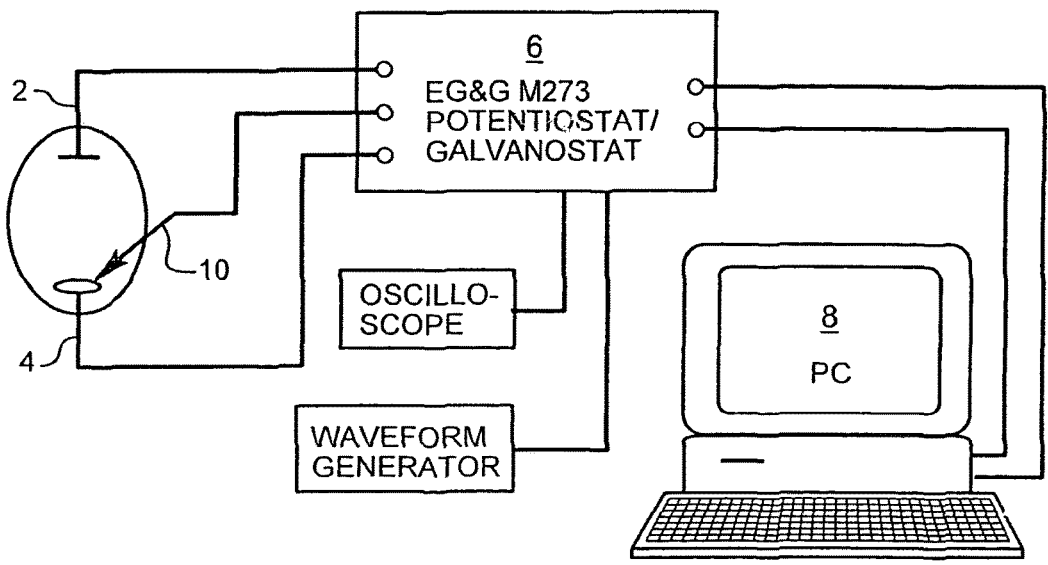
FIG. 12 shows an electroplating system with pulsed voltage control.
Figure 13:
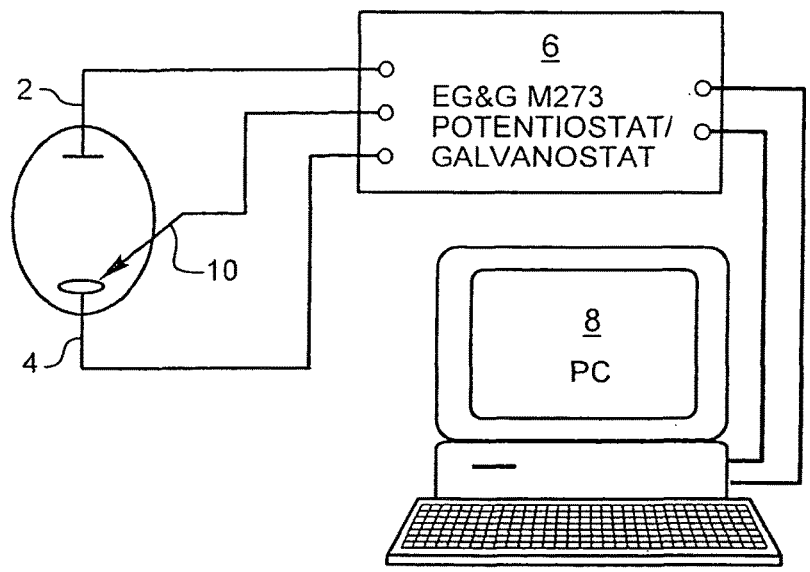
FIG. 13 shows an electroplating system with scanned voltage control.

Electroplating systems with pulsed current and pulsed voltage control are shown in FIGS. 9 and 10 respectively. While constant voltage, constant current, pulsed voltage or pulsed current can be used to control the electroplating process, constant voltage control of the plating process has been found to be most preferable. The most preferable voltage range to produce platinum gray has been found to be −0.45 Volts to −0.85 Volts. Applying voltage in this range with the above solution yields a plating rate in the range of about 1 μm per minute to 0.05 μm per minute, the preferred range for the plating rate of platinum gray. Constant voltage control also allows an array of electrodes in parallel to be plated simultaneously achieving a fairly uniform surface layer thickness for each electrode.

Figure 16:
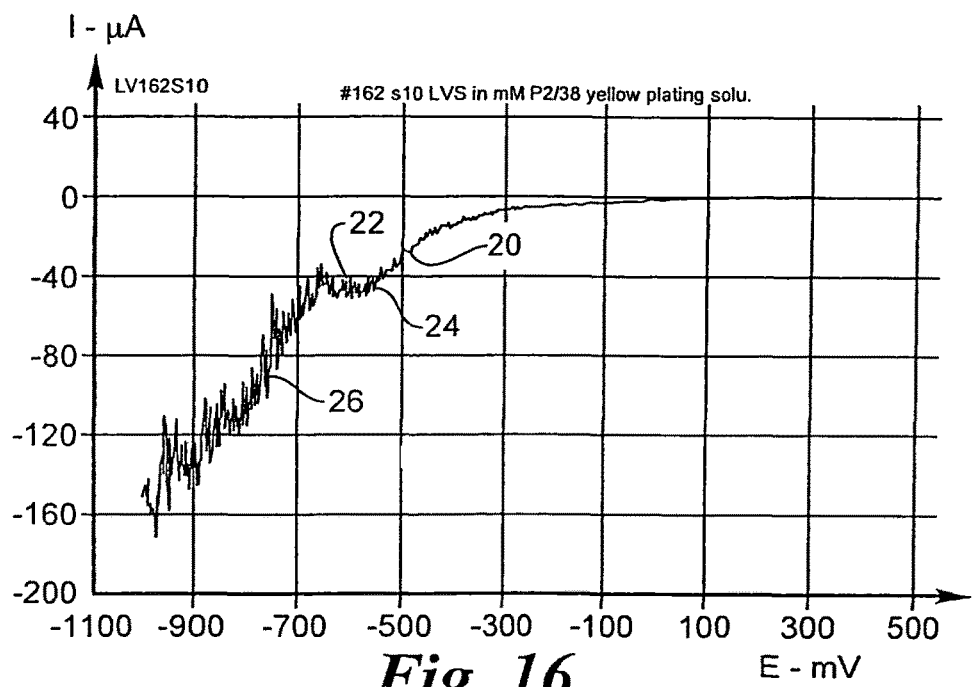
FIG. 16 shows a representative linear voltage sweep of a representative platinum gray electrode.
Figure 17:
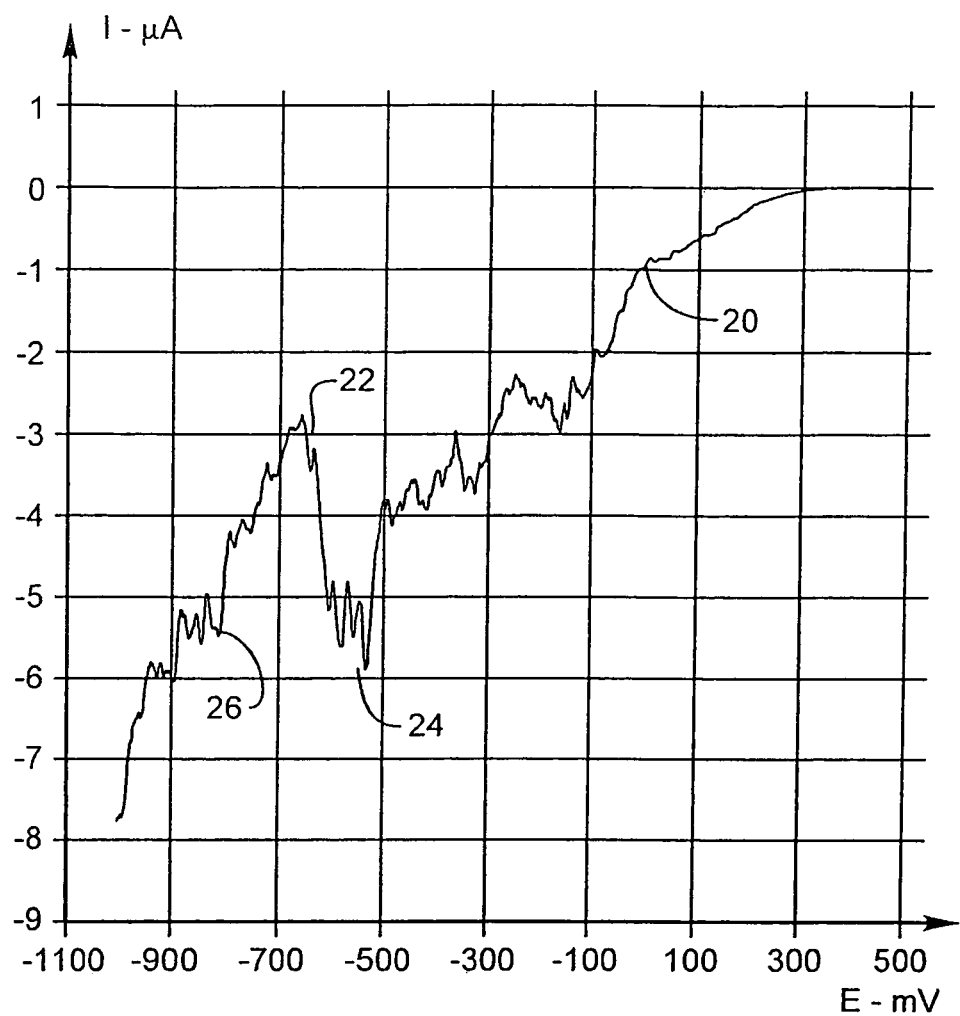
FIG. 17 shows a representative linear voltage sweep of a representative rough platinum electrode.

The optimal potential ranges for platinum gray plating are solution and condition dependent. Linear voltage sweep can be used to determine the optimal potential ranges for a specific plating system. A representative linear voltage sweep is shown in FIG. 16 for the fractal platinum gray surface and in FIG. 17 for non fractal rough platinum surface according to FIGS. 4 and 5. During linear voltage sweep, the voltage of an electrode is scanned cathodically until hydrogen gas evolution occurs which reveals plating rate control steps of electron transfer 20 and diffusion 22. For a given plating system, it is preferable to adjust the electrode potential such that the platinum reduction reaction has a limiting current under diffusion control or mixed control 24 between diffusion and electron transfer but that does not result in hydrogen evolution 26.

It is very difficult to plate shiny platinum in layers greater than approximately several microns because the internal stress of the dense platinum layer which will cause the plated layer to peel off and the underlying layers cannot support the above material. The additional thickness of the plate's surface layer allows the electrode to have a much longer usable life.

The following example is illustrative of electroplating platinum on a conductive substrate to form a platinum surface coating.

Figure 14:
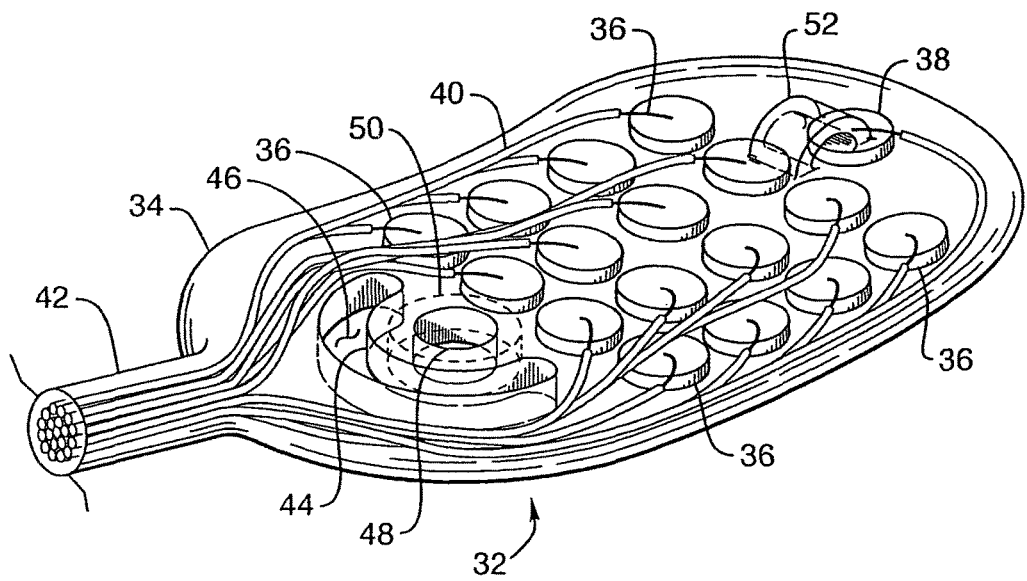
FIG. 14 shows an electrode platinum silicone array having 16 electrodes.

Electrodes with a surface layer of platinum are prepared in the following manner using constant voltage plating. An electrode platinum silicone array having 16 electrodes where the diameter of the platinum discs on the array range from 510 μm to 530 μm, as shown in FIG. 14, is first cleaned electrochemically in sulfuric acid and the starting electrode impedance is measured in phosphate buffered saline solution. Referring to FIG. 7, the electrodes are arranged in the electroplating cell such that the plating electrode 2 is in parallel with the common electrode 4. The reference electrode 10 is positioned next to the electrode 4. The plating solution is added to the electroplating cell 12 and the stirring mechanism 14 is activated.

A constant voltage is applied on the plating electrode 2 as compared to the reference electrode 10 using an EG&G PAR M273 potentiostat 6. The response current of the plating electrode 2 is recorded by a recording means 8. The response current is measured by the M273 potentiostat 6. After a specified time, preferably 1-90 minutes, and most preferably 30 minutes, the voltage is terminated and the electrode 4 is thoroughly rinsed in deionized water.

The electrochemical impedance of the electrode array with the surface coating of platinum is measured in a saline solution. The charge/charge density and average plating current/current density are calculated by integrating the area under the plating current vs. time curve. Scanning Electron Microscope (SEM)/Energy Dispersed Analysis by X-ray (EDAX™) analysis can be performed on selected electrodes. SEM Micrographs of the plated surface can be taken showing its fractal or rough surface. Energy Dispersed Analysis demonstrates that the sample is pure platinum rather than platinum oxide or some other materials.

The voltage range is most determinative of the formation of the fractal surface of platinum gray as shown in FIG. 1. For this system it is observed that the preferred voltage drop across the electrodes to produce platinum gray is approximately −0.55 to −0.65 Volts vs. Ag/AgCl reference electrode 10. The preferred platinum concentration for the plating solution is observed to be approximately 8 to 18 mM ammonium hexachloroplatinate in 0.4 M (Mole) disodium hydrogen phosphate.

The voltage range is determinative of the formation of the rough surface of platinum as shown in FIGS. 4 and 5. For this system it is observed that the preferred voltage drop across the electrodes to produce rough platinum is approximately −0.45 to −0.55 Volts vs. Ag/AgCl reference electrode 10. The preferred platinum concentration for the plating solution is observed to be approximately 3 mM to 30 mM $PtCl_4$ in sodium dihydrogen phosphate.

FIG. 14 provides a perspective view of a retinal electrode array for use with the present invention, generally designated 32, comprising oval-shaped electrode array body 34, a plurality of electrodes 36 made of a conductive material, such as platinum or one of its alloys, but that can be made of any conductive biocompatible material such as iridium, iridium oxide or titanium nitride, and a single reference electrode 38 made of the same material as electrode 36, wherein the electrodes are individually attached to separate conductors 40 made of a conductive material, such as platinum or one of its alloys, but which could be made of any biocompatible conductive material, that is enveloped within an insulating sheath 42, that is preferably silicone, that carries an electrical signal to each of the electrodes 36.

A strain relief internal tab 44, defined by a strain relief slot 46 that passes through the array body 34, contains a mounting aperture 48 for fixation of the electrode array body 34 to the retina of the eye or other neural interface by use of a surgical tack. A reinforcing ring 50 is colored and opaque to facilitate locating the mounting aperture 48 during surgery. A grasping handle 52 is located on the surface of electrode array body 34 to enable its placement by a surgeon using forceps or by placing a surgical tool into the hole formed by grasping handle 52. Grasping handle 52 avoids damage to the electrode body that might be caused by the surgeon grasping the electrode body directly. The electrode array 32 is described in greater detail in US Patent Application No. 2002/0111658 A1 filed Feb. 13, 2001 and entitled Implantable Retinal Electrode Array Configuration for Minimal Retinal Damage and Method of Reducing Retinal Stress, which is incorporated herein by reference.

Figure 15:
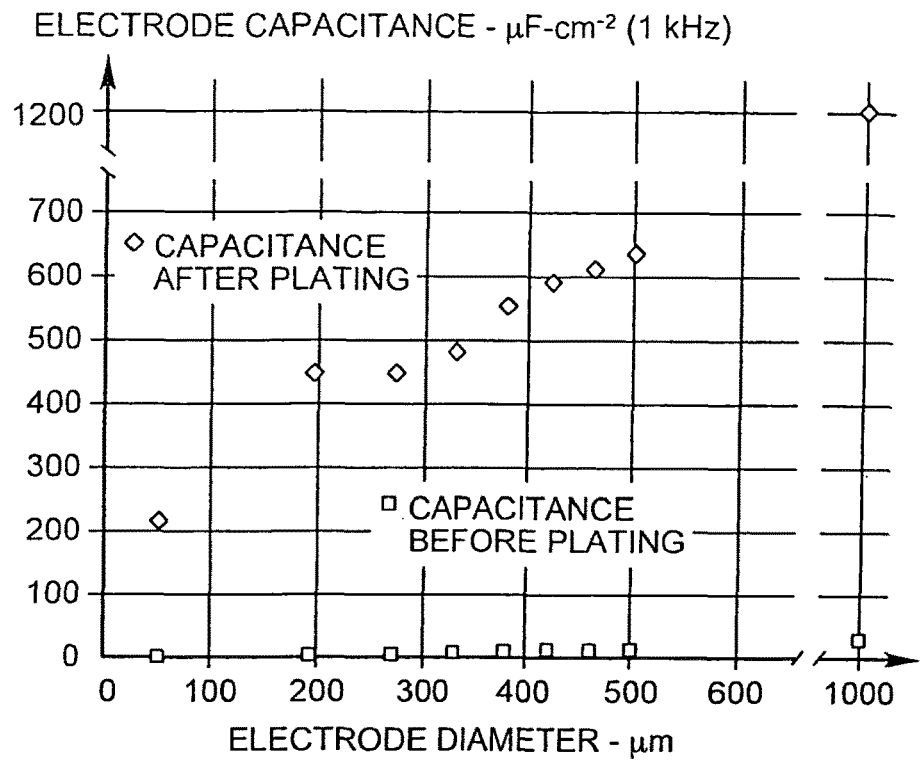
FIG. 15 shows the electrode capacitance for both plated and unplated electrodes of varying diameter.

FIG. 15 shows the increase in electrode capacitance of several electrodes of varying diameter for a polyimide array plated according to the above example at −0.6 V vs. Ag/AgCl Reference electrode for 30 minutes compared with unplated electrodes of the same diameters. Because the electrode capacitance is proportional to its surface area, the surface area increase, calculated from electrode capacitance, is 60 to 100 times that of shiny platinum for this array. It should be noted that shiny platinum exhibits some roughness and has a surface area increase up to 3 times that of the basic geometric shape. While it is simple to measure a surface area change between two sample using capacitance, it is difficult to compare a sample with the basic geometric shape.

As plating conditions, including but not limited to the plating solution, surface area of the electrodes, pH, platinum concentration and the presence of additives, are changed the optimal controlling voltage and/or other controlling parameters will also change according basic electroplating principles. Platinum gray will still be formed so long as the rate of deposition of the platinum particles is slower than that for the formation of platinum black and faster than that for the formation of shiny platinum.

The present invention provides a platinum coating with very regular particle shape and regular average size. The coating is thinner than known platinum coatings and has a rough surface which is mainly not porous with a large surface area. The coating of the present invention provides a good adherence between the substrate and the platinum coating. The platinum coated electrode is biocompatible and therefore implantable and provides less tissue reaction.

The present invention will be further explained in detail by the following examples.

EXAMPLE 1

Electroplating Platinum on a Conductive Substrate
Platinum Plating Solution Preparation 0.3 g sodium dihydrogen phosphate ($NaH_2PO_4$) and 6.03 g disodium hydrogen phosphate ($Na_2HPO_4$) [Fluka] were dissolved in 100 ml deionized water, and stirred by magnetic stirring for 30 minutes. The concentrations for $NaH_2PO_4$ and $Na_2HPO_4$ were 25 mM and 425 mM. Then 0.5 g of Platinum chloride ($PtCl_4$) [Alfa Aesar] was added to the phosphate solution to form the platinum salt concentrations of 15 mM. The solution was then stirred for 30 minutes. Different concentrations of ($PtCl_4$) were used in the experiments and the range of Pt salt concentrations was from 3 to 30 mM. The pH of the solution was measured at 7.9. The color of the solution was amber. The solution was deaerated before the plating process by bubbling nitrogen through the solution.

Preparation of the Substrate

A thin-film platinum polyimide array was used for platinum plating. The array included 16 electrodes with 200 um thin-film Pt disk as exposed electrode surface. All the electrodes in the array were shorted to common contact points for the plating. The Pt disk electrodes were first electrochemically cleaned by bubbling the surface with oxygen at +2.8V vs Ag/AgCl in 0.5 M $H_2SO_4$ for 10 sec. Then the surface was cleaned by bubbling with hydrogen at −1.2 V vs Ag/AgCl in 0.5 M $H_2SO_4$ for 15 sec to remove surface contaminations and polymer residues.

Electroplating Cell

A classical Pyrex glass three-electrode reaction cell was used for the electroplating. The reference electrode compartment was separated from the reaction compartment by a Vicor porous frit, in order to avoid the migration of concentrated KCl and AgCl from the inner filling solution of the reference electrode to the plating bath. The counter electrode was a platinized-platinum sheet of a real surface area equal to 1.8 $cm^2$.

A digital magnetic stirrer (Dataplate PMC720) was used to agitate the solution during plating. The solution temperatures were from 15° C. to 80° C. and were controlled by a VWR circulating water bath with a digital temperature controller (VWR 1147P).

The potential was controlled by using an EG&G PARC model 273 potentiostat-galvanostat and the response current, current density and charge were recorded by EG&G PARC M270 software. The charge/charge density and average plating current/current density were calculated by integrating the area under the plating current vs. time curve. The plating time was from 1 minute to 60 minutes.

Platinum Plating

A platinum polyimide electrode array having 16 electrodes (FIG. 14) having a diameter of 200 μm platinum disc on the array was cleaned electrochemically in 0.5 M $H_2SO_4$. The electrode array was placed in an electroplating cell containing a plating solution having a concentration of 15 mM platinum chloride in 0.025 M sodium dihydrogen phosphate and 0.425 M disodium hydrogen phosphate. The plating bath temperature was at 22° C. A constant voltage of −0.525 V vs Ag/AgCl reference electrode was applied on the electrode and terminated after 10 minutes. The electrode array was thoroughly rinsed in deionized water. The charge/charge density and average plating current/current density were calculated by integrating the area under the plating current vs. time curve. The current density was near linearly increased from initial 11.1 $A/cm^2$ to final 15.2 $A/cm^2$. The electrochemical capacitance of the electrode array with the surface coating of rough platinum was 1462 $\mu F/cm^2$, measured in a 10 mM phosphate buffered saline solution. The thin-film Pt disks only have an average capacitance of less than 20 $\mu F/cm^2$ before plating measured at the same condition. The optimal voltage drop across the electrodes for producing rough platinum was from −0.4 to −0.7 Volts vs. Ag/AgCl reference electrode. The plated platinum surface coating thickness is about 3.5 μm. The electrochemical active surface area increase is about 73 fold. The relation of surface area to the thickness of the platinum surface coating is 4.18 $F/cm^3$ [surface coating of rough platinum 1462 $\mu F/cm^2$ per thickness of the platinum coating of 3.5 μm.] The platinum surface coating adhesive strength was 55 mN.

Example 1 yields a platinum surface coating having a rough surface as shown in FIG. 4. The platinum coating contains particles with very regular particle shape and regular average size. The coating is thinner than known platinum coatings and has a rough surface which is mainly not porous with a large surface area. The coating provides a good adherence between the substrate and the platinum coating. The platinum coated electrode is biocompatible and therefore implantable and provides less tissue reaction.

EXAMPLE 2

Electroplating Platinum on a Conductive Substrate
Platinum Plating Solution Preparation 0.3 g sodium dihydrogen phosphate ($NaH_2PO_4$) and 6.03 g disodium hydrogen phosphate ($Na_2HPO_4$) [Fluka] were dissolved in 100 ml deionized water, and stirred by magnetic stirring for 30 minutes. The concentrations for $NaH_2PO_4$ and $Na_2HPO_4$ were 25 mM and 425 mM. Then 0.5 g of Platinum chloride ($PtCl_4$) [Alfa Aesar] was added to the phosphate solution to form the platinum salt concentrations of 15 mM. The solution was then stirred for 30 minutes and filtered to black solids. Different concentrations of ($PtCl_4$) were used in the experiments and the range of Pt salt concentrations was from 3 to 30 mM. The pH of the solution was measured at 7.9. The color of the solution was amber. The solution was deaerated before the plating process by bubbling nitrogen through the solution.

Preparation of the Substrate

A thin-film platinum polyimide array was used for platinum plating. The array included 16 electrodes with 200 μm thin-film Pt disk as exposed electrode surface. All the electrodes in the array were shorted to common contact points for the plating. The Pt disk electrodes were first electrochemically cleaned by bubbling the surface with oxygen at +2.8V vs Ag/AgCl in 0.5 M $H_2SO_4$ for 10 sec. Then the surface was cleaned by bubbling with hydrogen at −1.2 V vs Ag/AgCl in 0.5 M $H_2SO_4$ for 15 sec to remove surface contaminations and polymer residues.

Electroplating Cell

A classical Pyrex glass three-electrode reaction cell was used for the electroplating. The reference electrode compartment was separated from the reaction compartment by a Vicor porous frit, in order to avoid the migration of concentrated KCl and AgCl into the inner filling solution of the reference electrode. The counter electrode was a platinized-platinum sheet of a real surface area equal to 1.8 $cm^2$.

A digital magnetic stirrer (Dataplate PMC720) was used to agitate the solution during plating. The solution temperatures were from 15° C. to 80° C. and were controlled by a VWR circulating water bath with a digital temperature controller (VWR 1147P).

The potential was controlled by using an EG&G PARC model 273 potentiostat-galvanostat and the response current, current density and charge were recorded by EG&G PARC M270 software. The charge/charge density and average plating current/current density were calculated by integrating the area under the plating current vs. time curve. The plating time was from 1 minute to 60 minutes.

Platinum Plating

A platinum polyimide electrode array having 16 electrodes (FIG. 14) having a diameter of 200 μm platinum disc on the array was cleaned electrochemically in 0.5 M $H_2SO_4$. The electrode array was placed in an electroplating cell containing a plating solution having a concentration of 15 mM platinum chloride in 0.025 M sodium dihydrogen phosphate and 0.425 M disodium hydrogen phosphate. The plating bath temperature was at 22° C. A constant voltage of −0.5 V vs Ag/AgCl reference electrode was applied on the electrode and terminated after 10 minutes. The electrode array was thoroughly rinsed in deionized water. The charge/charge density and average plating current/current density were calculated by integrating the area under the plating current vs. time curve. The current density was near linearly increased from initial 10.8 $A/cm^2$ to final 14.6 $A/cm^2$. The electrochemical capacitance of the electrode array with the surface coating of rough platinum was 1417 $\mu F/cm^2$, measured in a 10 mM phosphate buffered saline solution. The thin-film Pt disks only have an average capacitance of less than 20 $\mu F/cm^2$ before plating measured at the same condition. The optimal voltage drop across the electrodes for producing rough platinum was from −0.4 to −0.7 Volts vs. Ag/AgCl reference electrode. The plated platinum surface coating thickness is about 2.5 μm. The electrochemical active surface area increase is about 70 fold. The relation of surface area to the thickness of the platinum surface coating is 5.67 $F/cm^3$ [surface coating of rough platinum 1417 $\mu F/cm^2$ per thickness of the platinum coating of 2.5 μm.] The platinum surface coating adhesive strength was 58 mN.

Example 2 yields a platinum surface coating having a rough surface as shown in FIG. 5. The platinum coating contains particles with very regular particle shape and regular average size. The coating is thinner than known platinum coatings and has a rough surface which is mainly not porous with a large surface area. The coating provides a good adherence between the substrate and the platinum coating. The platinum coated electrode is biocompatible and therefore implantable and provides less tissue reaction.

EXAMPLE 3

Electroplating Platinum Gray on a Conductive Substrate

A platinum polyimide electrode array having 16 electrodes (FIG. 14) having a diameter of 200 um platinum disc on the array was cleaned electrochemically in 0.5 M $H_2SO_4$. The electrode array was placed in an electroplating cell containing a plating solution having a concentration 20 mM ammonium hexachloroplatinate, 0.025 M sodium dihydrogen phosphate and 0.425 M disodium hydrogen phosphate. The voltage of −0.65 V was terminated after 30 minutes. The electrode was thoroughly rinsed in deionized water. The electrochemical capacitance of the electrode with the surface coating of platinum gray was 1200 $\mu F/cm^2$, measured in a 10 mM phosphate buffered saline solution. The charge/charge density and average plating current/current density were calculated by integrating the area under the plating current vs. the time curve. The optimal voltage drop across the electrodes for producing platinum gray was from −0.55 to −0.75 Volts vs. Ag/AgCl reference electrode.

The platinum coating showed the following properties:
platinum surface coating thickness: 11.0 μm;
electrochemical active surface area increase: 60 fold;
platinum surface coating adhesive strength: 50 mN; and
platinum surface coating color density: 1.0 D.

Example 3 yields a platinum surface coating having a fractal surface as shown in FIG. 1. The relation of surface area to the thickness of the platinum surface coating is 1.09 $F/cm^3$ [surface coating of rough platinum 1200 $\mu F/cm^2$ per thickness of the platinum coating of 11.0 μm.] The coating provides a good adherence between the substrate and the platinum coating. The platinum coated electrode is biocompatible and therefore implantable and provides less tissue reaction.

The plating conditions and properties of the platinum coatings performed in Examples 1 to 3 are summarized in the following table 1.

TABLE 1

| Conditions and Properties | Example 1 Rough Pt | Example 2 Rough Pt | Example 3 Fractal Pt |
|---|---|---|---|
| Plating Agent | 15 mM $PtCl_4$ | 15 mM $PtCl_4$ | 20 mM $NH_4[PtCl_6]$ |
| Plating Solution | 0.025 M $NaH_2PO_4$ and 0.425 M $Na_2HPO_4$ | | |
| Initial Capacitance | 20 $\mu F/cm^2$ | 20 $\mu F/cm^2$ | 20 $\mu F/cm^2$ |
| Temperature | 22° C. | 22° C. | 22° C. |
| Voltage vs. Ag/AgCl Reference Electrode | −0.525 V | −0.5 V | −0.6 V |
| Time | 10 minutes | 10 minutes | 30 minutes |
| Final Capacitance | 1462 $\mu F/cm^2$ | 1417 $\mu F/cm^2$ | 1200 $\mu F/cm^2$ |
| Thickness | 3.5 μm | 2.5 μm | 11.0 μm |
| Surface Area Increase | 73 fold | 70 fold | 60 fold |
| Adhesive Strength | 55 mN | 58 mN | 50 mN |
| Surface Coating/Surface Thickness | 4.18 $F/cm^3$ | 5.67 $F/cm^3$ | 1.09 $F/cm^3$ |
| Current Density Initial to Final Linear Increase | 11.1 $A/cm^2$ to 15.2 $A/cm^2$ | 10.8 $A/cm^2$ to 14.6 $A/cm^2$ | 15.1 $A/cm^2$ to 24.5 $A/cm^2$ |
| Voltage Drop Across the Electrodes | −0.4 V to −0.7 V | −0.4 V to −0.7 V | −0.55 V to −0.75 V |
| Substrate Platinum Disc Diameter | 200 μm | 200 μm | 200 μm |

While the invention has been described by means of specific embodiments and applications thereof, it is understood that numerous modifications and variations could be

What I claim is:

1. A method of forming a non-porous platinum coating on a platinum substrate having a basic geometric shape, the platinum coating having a rough surface and grains, comprising the steps of:

selecting an electroplating solution having a basic pH and containing $Na_2HPO_4$, $NaH_2PO_4$, and $PtCl_4$;

selecting a power source and connecting an anode, a reference electrode, and a cathode to said power source;

placing said anode, said cathode, said reference electrode for use as a reference in controlling said power source, and said electroplating solution in an electroplating cell;

agitating said electroplating solution;

electroplating for about 10 minutes at a rate of 0.25 to 0.35 micrometers per minute to form a non-porous biocompatible platinum coating on said cathode by supplying power to said cathode, said power having an electrode constant voltage, and stopping plating after achieving a thickness of 2.5 micrometers to 3.5 micrometers;

wherein said step of electroplating said non-porous biocompatible platinum coating is electroplating a surface of a rough configuration, having regular bead shaped particles with particle sizes ranging between 0.1 micrometer and 2.0 micrometers in size on said cathode, and an increase in surface area of 70 to 73 times of a surface area defined by the basic geometric shape, within the thickness of 2.5 micrometers to 3.5 micrometers.

2. The method of claim 1 wherein said step of electroplating is controlled by said electrode constant voltage.

3. The method of claim 1 wherein said step of electroplating is partially diffusion limited and is controlled by said electrode constant voltage.

4. The method of claim 1 wherein said step of electroplating is performed in said basic electroplating solution at a pH of 7.9 and not in an acidic electroplating solution.

5. The method of claim 1 wherein said step of electroplating is performed lead-free.

* * * * *